United States Patent [19]

Steiner

[11] Patent Number: 4,983,402

[45] Date of Patent: Jan. 8, 1991

[54] ORALLY ADMINISTERABLE ANF

[75] Inventor: Solomon S. Steiner, Mt. Kisco, N.Y.

[73] Assignee: Clinical Technologies Associates, Inc., Elmsford, N.Y.

[21] Appl. No.: 315,393

[22] Filed: Feb. 24, 1989

[51] Int. Cl.$^5$ ............................................. A61K 9/50
[52] U.S. Cl. ................................. 424/491; 424/455
[58] Field of Search ................ 530/841, 813, 812; 424/450, 491; 514/21, 869

[56] References Cited

U.S. PATENT DOCUMENTS

| 3,052,655 | 9/1962 | Fox et al. | 260/78 |
|---|---|---|---|
| 3,076,790 | 2/1963 | Fox et al. | 260/78 |
| 3,576,758 | 4/1971 | Emrick | 252/316 |
| 3,794,561 | 2/1974 | Matsukawa et al. | 530/841 |
| 3,822,348 | 7/1974 | Higashi et al. | 424/95 |
| 3,962,416 | 6/1976 | Katzen | 426/103 X |
| 4,061,466 | 12/1977 | Sjöhölm et al. | 530/813 X |
| 4,217,370 | 8/1980 | Rawlings | 426/98 |
| 4,272,506 | 6/1981 | Schwarzberg | 530/813 X |
| 4,351,337 | 9/1982 | Sidman | 128/260 |
| 4,388,304 | 6/1983 | Nyéki; et al. | 530/800 X |
| 4,492,684 | 1/1985 | Goosen et al. | 424/19 |
| 4,647,455 | 3/1987 | De Bold | 514/869 X |
| 4,671,954 | 6/1987 | Goldberg et al. | 424/450 |
| 4,703,042 | 10/1987 | Bodor | 514/822 X |
| 4,753,804 | 6/1988 | Iaccheri et al. | 424/499 |
| 4,757,024 | 7/1988 | Roper | 530/812 X |
| 4,774,320 | 9/1988 | Tagliabue et al. | 530/328 |
| 4,789,734 | 12/1988 | Pierschbacher | 530/841 X |
| 4,844,904 | 7/1989 | Hamaguchi et al. | 424/450 |

FOREIGN PATENT DOCUMENTS

| 78300208.2 | 2/1979 | European Pat. Off. . |
| 2424169 | 12/1974 | Fed. Rep. of Germany . |
| 2565102 | 6/1984 | France . |
| 58-035111 | 3/1983 | Japan . |

OTHER PUBLICATIONS

Przybylski and Fox, *Appl. Biochem. Biotech.* 10, 301–307 (1964).
Matsuno, *BioSystems* 17, 11–14 (1984).
Kokufuta, et al., *BioSystems* 16, 175–181 (1984).
Sun, et al., *Chemical Abstract* 105:12027p (Pharmaceuticals vol. 105, 1986).

*Primary Examiner*—Thurman K. Page
*Attorney, Agent, or Firm*—Kilpatrick & Cody

[57] ABSTRACT

Atrial naturiuretic factor (ANF) is encapsulated within hollow acidic proteinoid microspheres which are stable and protective in the acidic stomach of a mammal but which dissolve at the near neutral pH of the blood. Microspheres having diameters of less than about 10 microns readily penetrate the gastrointestinal mucosa and release the ANF in the bloodstream in physiologically active form. Such gastric administration significantly extends the period of effectiveness of ANF as a diuretic and blood pressure suppressant.

6 Claims, No Drawings

ORALLY ADMINISTERABLE ANF

BACKGROUND OF THE INVENTION

1. Field of the Invention

This invention relates to atrial natriuretic factor which is encapsulated within acidic proteinoid microspheres and to the periodic oral administration of same to warm blooded animals to control blood pressure.

2. Description of the Prior Art

Atrial natriuretic factor, which is commonly abbreviated ANF, is a polypeptide material which is believed to be produced in the atrium of the mammalian heart and which is known to be a powerful diuretic and blood pressure regulator. Because of the minute quantities of ANF found in mammals, it has been difficult to extract sufficient quantities from domestic animal carcasses to comprehensively study the effect of administering ANF to living mammals and totally impractical to use such animal extract as a primary diuretic and blood pressure depressant. However, genetically engineered ANF has recently become available in larger quantities and extensive research has been undertaken on the therepeutic use of this material.

Similar to many other endogenous polypeptides, unprotected ANF is rapidly degraded in the gastrointestinal tract and is absorbed poorly through the gastrointestinal mucosa. Its administration has, heretofore, been limited to intravenous injection.

Recent studies have shown that the intravenous administration to hypertensive rats of single large doses of ANF produce initial large reductions in blood pressure, but that this effect is transient. Significant reductions in blood pressure have been achieved for periods that seldom exceed about twenty minutes and, regardless of dosage, blood pressures return to essentially pre-dosage levels in less than thirty minutes. This exceedingly short duration of effectiveness has been attributed to the fact that ANF in the bloodstream is rapidly inactivated or removed by the kidneys. Thus, in order to maintain the effective presence of ANF in the bloodstream, it has been found that it must be repeatedly injected at short intervals and that its anti-hypertensive effect is most pronounced when continuously infused.

This obviously is not practical for chronic therapy and there is a need for a means for delivering ANF to the bloodstream which will sustain it at an effective level for reducing blood pressure for a period that is sufficiently long to permit periodic administration at reasonable intervals.

U.S. patent application Ser. No. 98,027, issued as U.S. Pat. No. 4,925,673 the disclosure of which is incorporated herein by reference, describes orally administerable compositions for delivering a gastrointestinally labile or poorly absorbed pharmacological agent to the bloodstream in physiologically active form. The active agent in these compositions is microencapsulated within hollow acidic proteinoid microspheres which are stable in acid environments and resistant to gastrointestinal enzymes, but which dissolve at the near neutral pH of the blood. These hollow microspheres protect the encapsulated pharmacological agent in the acidic portions of the gastrointestinal tract and those microspheres having a diameter of less than about 10 microns readily penetrate the gastrointestinal mucosa and release the agent in the bloodstream.

SUMMARY OF THE INVENTION

It is an objective of this invention to provide a means for orally administering ANF which will deliver it to the bloodstream in physiologically active form. It is a further object of this invention to prolong the blood pressure depressant effect of ANF for a period sufficient to permit periodic dosages at reasonable intervals.

These objects and other advantages, which will be apparent from this specification, are achieved by the invention described below.

It now has been demonstrated that ANF, which is encapsulated within acidic proteinoid microspheres having diameters less than about 10 microns and orally administered to mammals, delivers a far greater amount of physiologically active ANF to the bloodstream than similar doses of unencapsulated ANF. Unexpectedly, it also has been found that a single such oral microencapsulated dosage prolongs the duration of the effective reduction in systolic blood pressure in hypertensive animals by a factor of four to ten or more as compared to much larger single doses of IV administered ANF.

One aspect of this invention is a delivery system for ANF comprising that blood pressure regulator encapsulated within acidic proteinoid microspheres having diameters less than about 10 microns and preferably being predominantly from about 0.1 to about 5.0 microns.

Another aspect of this invention is a method for treating hypertension in a mammal comprising orally administering to said mammal an effective quantity of ANF encapsulated within acidic proteinoid microspheres having diameters less than about 10 microns and preferably being predominantly from about 0.1 to about 5.0 microns.

DESCRIPTION OF PREFERRED EMBODIMENTS

The ANF bearing acidic proteinoid microspheres of this invention are suitably made by any of the procedures described in Ser. No. 98,027 issued as U.S. Pat. No. 4,925,673; e.g., by mixing ANF with water, acidifying the mixture to a pH at which the acidic proteinoid is insoluble, contacting the pH adjusted mixture with that powdered proteinoid and recovering the spontaneously formed microspheres.

As in Ser. No. 98,027 issued as U.S. Pat. No. 4,925,673, the preferred acidic proteinoid materials for use in this invention are thermal condensation polymers derived from at least one acidic amino acid and at least one other acidic, basic or neutral amino acid. Although microsphere forming polymers can be derived from as few as two such amino acids, a greater diversity generally results in higher yields of uniform size microspheres. Proteinoids derived exclusively from naturally occurring amino acids (i.e., those found in animal or vegetable protein, including optical isomers thereof) are especially preferred as it has been shown that when such proteinoids dissolve in human serum or in the bloodstreams of rats and guinea pigs, they consistently break into low molecular weight fragments which produce no toxic or immunological response.

EXAMPLE 1

A flask equipped with an electric heating mantle and containing equimolar quantities of anhydrous aspartic acid, glutamic acid, valine and glycine is heated at approximately 175° C. under a stream of nitrogen until the contents are molten. The nitrogen swept mixture then is agitated gently with a glass encased magnetic stirrer and the temperature is raised to and held at 180° C. for six hours. After cooling, the dark amber product is extracted with saturated aqueous sodium bicarbonate and the extract dialyzed through a cellulose membrane against distilled water at room temperature for 24 hours, the water being changed every four hours. The entire content of the dialysis tubes then is dried under vacuum at 65° and the residual solids are ground to a fine powder with mortar and pestle. An aqueous solution of proteinoid is produced by mixing 35 mg of this powder per ml of water, adjusting the pH to 7.4 with concentrated aqueous sodium bicarbonate and removing any insoluble materials by filtration.

EXAMPLE 2a

Sufficient distilled water is added to cloned bovine ANF provided by California Biotechnics Corporation to produce a mixture containing 0.4 mg of ANF per ml and the mixture is adjusted to pH 3.5 with concentrated acetic acid. A portion of this mixture is diluted with an equal volume of pH 3.5 aqueous acetic acid to reduce the ANF concentration to 0.2 mg/ml and 1 ml samples are set aside for use in Experiments 3 and 4.

EXAMPLE 2b

One part by volume of the solids free proteinoid solution of Example 1 is rapidly injected into an equal volume of the 0.4 mg/ml aqueous mixture of unprotected ANF of Example 2a. The resulting mixture, which has a pH of approximately 4.5, is chilled in an ice bath for 15 minutes and filtered to recover the resulting ANF filled microspheres. These are washed with pH 3.5 aqueous acetic acid and 0.4 mg of the microspheres are made up to one volume by the addition of pH 3.5 aqueous acetic acid. Microscopic examination of the resulting suspension reveals that the microspheres are predominately from about 0.1 to about 5.0 microns in diameter. One ml samples of this suspension of microencapsulated ANF, which contain slightly less than 0.2 mg/ml of ANF, are set aside for use in Examples 3 and 4.

EXAMPLE 3

Four normal young male rats are selected arbitrarily for this experiment. Each of rats A and B is administered by gavage one ml of the 0.2 mg/ml unprotected ANF of Example 2a and each of rats C and D is similarly given a one ml dosage of the suspension of microencapsulated ANF of Example 2b. Blood samples are withdrawn from the tails of the animals 90 minutes after administration and the ANF levels in the serum are determined by radioimmunoassay. This assay distinguishes between natural rat ANF and the cloned bovine ANF that was administered. The bovine ANF levels in rats A and B are 28 and 62 fmol/ml (fempto moles per milliliter), while those of rats C and D are 360 and 365 fmol/ml.

These results demonstrate that the quantity of orally administered ANF that is delivered to the bloodstream is greatly increased by microencapsulation in acidic proteinoid microspheres which are stable to stomach acidity and dissolve at the near neutral pH of the blood and which have diameters of less than about 10 microns so as to readily penetrate the gastrointestinal mucosa.

EXAMPLE 4

Six hypertensive male rats weighing about 500 g each are arbitrarily divided into three groups of two. Each of the animals of group 1 is administered by gavage 1 ml of the suspension of microencapsulated ANF of Example 2b. Those of group 2 each similarly receive 1 ml of a similar suspension of proteinoid microspheres which contain no ANF and which are made by omitting ANF from the procedure of Example 2b. Those of group 3 each similarly receive 1 ml of pH 3.5 aqueous acetic acid. Blood pressure measurements are made on the animals immediately before and at intervals after administration of their doses. Table 1 shows the average systolic blood pressures for the groups.

TABLE 1

| | Systolic Blood Pressure (mm Hg) | | |
|---|---|---|---|
| | Time after Dosage (minutes) | | |
| | 0 | 15 | 90 |
| Group 1 - Microencapsulated ANF | 207 | 175 | 178 |
| Group 2 - Microcapsules only | 198 | 195 | 197 |
| Group 3 - pH 3.5 aqueous acetic acid | 185 | 189 | 188 |

These results demonstrate the unexpected prolongation of the blood pressure suppressing effect when ANF is delivered to the bloodstream by oral administration of same encapsulated within less than 10 micron diameter acidic proteinoid microspheres.

It will be apparent to those of ordinary skill in the art that numerous changes and modifications can be made in the illustrative embodiments of the invention described above without departing from the spirit and scope of the invention as set forth in the following claims.

I claim:

1. Orally administerable composition for regulating mammalian blood pressure comprising atrial natriuretic factor encapsulated within acidic proteinoid microspheres having diameters of less than about 10 microns and formed of thermal condensation polymers of mixed amino acids.

2. Composition of claim 1 wherein said microspheres are predominantly from about 0.1 to about 5.0 microns in diameter.

3. Composition of claim 1 wherein said acidic proteinoid is a thermal condensation polymer derived from at least one acidic amino acid selected from glutamic acid and aspartic acid and at least one other naturally occuring amino acid.

4. Orally administerable composition for delivering atrial natriuretic factor to the bloodstream of a mammal in physiologically active and long lasting form comprising said atrial natriuretic factor encapsulated within acidic proteinoid microspheres having diameters predominantly from about 0.1 to about 5.0 microns, said proteinoid being a thermal condensation polymer derived from about one mol part of acidic amino acid selected from glutamic acid, aspartic acid and mixtures thereof and about one mol part of another amino acid selected from naturally occurring basic and neutral amino acids and mixtures thereof.

5. Composition of claim 4 wherein said proteinoid is derived from about equimolar parts of glutamic acid, aspartic acid, valine and glycine.

6. Method for regulating mammalian blood pressure comprising the periodic oral administration to said mammal of a physiologicallly effective amount of atrial natriuretic factor encapsulated within acidic proteinoid microspheres, said acidic proteinoid being stable to stomach acid and unstable at the near neutral pH of the blood, said microspheres being formed of thermal condensation polymers, and said microspheres being less than about 10 microns in diameter.

* * * * *